United States Patent [19]

Tekamp-Olson et al.

[11] Patent Number: 5,814,484
[45] Date of Patent: Sep. 29, 1998

[54] EXPRESSION OF MACROPHAGE INDUCIBLE PROTEINS (MIPS) IN YEAST CELLS

[76] Inventors: Patricia Tekamp-Olson, 80 Camino de Herrera, San Anselmo, Calif. 94960; Carol Ann Gallegos, 605 Carmel Ave., Albany, Calif. 94706

[21] Appl. No.: 383,691

[22] Filed: Jan. 31, 1995

Related U.S. Application Data

[63] Continuation of Ser. No. 951,321, Sep. 25, 1992, abandoned, which is a continuation of Ser. No. 582,636, Sep. 14, 1990, abandoned.

[51] Int. Cl.$^6$ .............................. C12N 1/19; C12N 15/19; C12N 15/67; C12N 15/81
[52] U.S. Cl. .................... 435/69.9; 435/69.8; 435/254.2; 536/235; 536/24.1
[58] Field of Search ............................... 435/69.9, 172.3, 435/320.1, 254.2, 69.8; 530/351; 536/23.5, 24.1

[56] References Cited

U.S. PATENT DOCUMENTS 5,171,844  12/1992  Van Ooyen ............................ 530/383

FOREIGN PATENT DOCUMENTS

| 0 310 136 | 5/1989 | European Pat. Off. . |
| 0324274 | 7/1989 | European Pat. Off. . |
| WO 90/07009 | 6/1990 | WIPO . |
| WO 91/04274 | 4/1991 | WIPO . |

OTHER PUBLICATIONS

Nakao et al., Molecular and Cellular Biology 10(7):3646–3658 (1990).

Wolpe, et al. (1987), J. Exp. Med., 167:570–581, "Macrophages secrete a novel heparin–binding protein with inflammatory and neutrophil chemokinetic properties".

Sherry, et al. (1988), J. Exp. Med., 168:2251–2259, "Resolution of the two components of macrophage inflammatory protein 1, and cloning and characterization of one of those components, macrophage inflammatory protein 1 beta."

Davatelis, et al. (1988), J. Exp. Med., 167:1939–1944, "Cloning and characterization of a cDNA for murine macrophage inflammatory protein (MIP), a novel monokine with inflammatory and chemokinetic properties."

Brown, et al. (1989), J. Immunol., 142:678–687, "A family of small inducible proteins secreted by leukocytes are members of a new superfamily that includes leukocytes and fiberglass–derived inflammatory agents, growth factors, and indicators of various activation processes."

Kwon, et al. (1989), Proc. Natl. Acad. Sci. USA, 86:1963–1967, "cDNA sequences of two inducible T–cell genes."

Obaru, et al. (1986), J. Biochem., 99:885–894, "A cDNA clone used to study mRNA inducible in human tonsillar lymphocytes by a tumor promoter."

Zipfel, et al. (1989), J. Immunol., 142:1582–1590, "Mitogenic activation of human T cells induces two closely related genes which share structural similarities with a new family of secreted factors."

Lipes, et al. (1988), Proc. Natl. Acad. Sci. USA, 85:9704–9708, "Identification, cloning, and characterization of an immune activation gene."

Miller, et al. (1989), J. Immunol., 143:2907, "A novel polypeptide secreted by activated human T lymphocytes."

Richmond, et al. (1988), EMBO J., 7:2025–2033, "Molecular characterization and chromosomal mapping of melanoma growth stimulatory activity, a growth factor structurally related to B–thromboglobulin."

Oquendo, et al. (1989), J. Biol. Chem., 264:4133–4137, "The platelet–derived growth factor–inducible KC gene encodes a secretory protein related to platelet alpha–granule proteins."

Graham, et al. (1990), Nature, 344:442, "Identification and characterization of an inhibitor of haemopoletic stem cell proliferation."

Yamamura, et al., (1989), J. Clin. Invest., 84:1707, "Synthesis of a novel cytokine and its gene (LD78) expressions in Hematopoletic fresh tumor cells and cell lines."

Rollins, et al. (1988), Proc. Nat. Acad. Sci. USA, 85:3738, "Cloning and expression of JE, a gene inducible by platelet–derived growth factor and whose product has cytokine–like properties."

Mullenbach, et al. (1986), J. Biol. Chem., 261:719, "Chemical synthesis and expression in yeast of a gene encoding connective tissue activating peptide–III."

Luster, et al. (1987), J. Exp. Med., 166:1084, "Biochemical characterization of a γ interferon–inducible cytokine (IP–10)."

Maione, et al. (1990), Science, 247:77, "Inhibition of angiogenesis by recombinant human platelet factor–4 and related peptides."

Lindley, et al. (1988), Proc. Natl. Acad. Sci. USA, 85:9199, "Synthesis and expression in Escherichia coli of the gene encoding monocyte–derived neutrophil–activating factor: biological equivalence between natural and recombinant neutrophil–activating factor."

Furuta, et al. (1989), J. Biochem., 106:436, "Production and characterization of recombinant human neutrophil chemotactic factor."

Gimbrone, et al. (1989), Science, 246:1601, "Endothelial interleukin–8: a novel inhibitor of leukocyte–endothelial interactions."

(List continued on next page.)

*Primary Examiner*—Dian C. Jacobson
*Attorney, Agent, or Firm*—W. Murray Spruill; Ling-Fong Chung; Robert P. Blackburn

[57] ABSTRACT

Methods for the expression of mammalian MIP-1α and MIP-1β are disclosed. The methods generally comprise introducing into a yeast cell, a DNA molecule capable of directing the expression and if desired the secretion of either MIP-1α or MIP-1β. Methods for expression of constructs encoding both MIP-1α and MIP-1β are also described. The MIP molecules so produced are biologically active.

11 Claims, 3 Drawing Sheets

OTHER PUBLICATIONS

Broxmeyer, et al. (1989, J. Exp. Med.,170:1583, "Myelopoietic enhancing effects of murine macrophage inflammatory proteins 1 and 2 on colony formation in vitro by murine and human bone marrow granulocyte/macropage progenitor cells."

Pennica, D. et al. *Nature* 301:214–220 (1983).

Mullenbach, G. T., et al. *J. Biol. Chem.* 261:719–722 (1986).

Old, R. W., et al. *Principles of Gene Manipulation* (1989) pp. 164–165.

Brake, A. J., et al. *PNAS* 81:4642–4646, (1984)

Human MIP-1α Cdna

```
                                           -22             -20
                                       Met Gln Val Ser Thr Ala Ala Leu
CCACATTCCGTCACCTGCTCAGAATC             ATG CAG GTC TCC ACT GCT GCC CTT

-10                                                         1
Ala Val Leu Leu Cys Thr Met Ala Leu Cys Asn Gln Phe Ser Ala
GCT GTC CTC CTC TGC ACC ATG GCT CTC TGC AAC CAG TTC TCT GCA

10
Ser Leu Ala Ala Asp Thr Pro Thr Ala Cys Cys Phe Ser Tyr Thr
TCA CTT GCT GCT GAC ACG CCG ACC GCC TGC TGC TTC AGC TAC ACC 20                                          30
Ser Arg Gln Ile Pro Gln Asn Phe Ile Ala Asp Tyr Phe Glu Thr
TCC CGG CAG ATT CCA CAG AAT TTC ATA GCT GAC TAC TTT GAG ACG

40
Ser Ser Gln Cys Ser Lys Pro Gly Val Ile Phe Leu Thr Lys Arg
AGC AGC CAG TGC TCC AAG CCC GGT GTC ATC TTC CTA ACC AAG CGA 50                                          60
Ser Arg Gln Val Cys Ala Asp Pro Ser Glu Glu   Trp Val Gln Lys
AGC CGG CAG GTC TGT GCT GAC CCC AGT GAG GAG   TGG GTC CAG AAA

70
Tyr Val Ser Asp Leu Glu Leu Ser Ala OP
TAT GTC AGC GAC CTG GAG CTG AGT GCC TGA GGGGTCCAGAAGCTTCGAGG
CCCAGCGACCTCGGTGGGCCAGTGGGGAGGAGCAGGAGCCTGAGCCTTGGGAACATGCGT
                 +100
GTGACCTCCACAGCTACCTCTTCTATGGACTGGTTGTTGCCAAACAGCCACACTGTGGGA
                                                          +200
CTCTTCTTAACTTAAATTTTAATTTATTTATACTATTTAGTTTTGTAATTTATTTTCGA
TTTCACAGTGTGTTTGTGATTGTTTGCTCTGAGAGTTCCCCTGTCCCCTCCCCCTTCCCT
                                   +300
CACACCGCGTCTGGTGACAACCGAGTGGCTGTCATCAGCCTGTGTAGGCAGTCATGGCAC
CAAAGCCACCAGACTGACAAATGTGTATCGGATGCTTTTGTTCAGGGCTGTGATCGGCCT
                 +400
GGGGAAATAATAAAGATGCTCTTTTAAAA
```

FIG. 1

Human-MIP-1β

```
                                                     -23          -20
   •          •          •                       Met Lys Leu Cys Val
AGCCTCACCTCTGAGAAAACCTCTTTTCCACCAATACC            ATG AAG CTC TGC GTG

-10
Thr Val Leu Ser Leu Leu Met Leu Val Ala Ala Phe Cys Ser Pro
ACT GTC CTG TCT CTC CTC ATG CTA GTA GCT GCC TTC TGC TCT CCA 1                                   10
Ala Leu Ser Ala Pro Met Gly Ser Asp Pro Pro Thr Ala Cys Cys
GCG CTC TCA GCA CCA ATG GGC TCA GAC CCT CCC ACC GCC TGC TGC

20
Phe Ser Tyr Thr Ala Arg Lys Leu Pro Arg Asn Phe Val Val Asp
TTT TCT TAC ACC GCG AGG AAG CTT CCT CGC AAC TTT GTG GTA GAT 30                                  40
Tyr Tyr Glu Thr Ser Ser Leu Cys Ser Gln Pro Ala Val Val Phe
TAC TAT GAG ACC AGC AGC CTC TGC TCC CAG CCA GCT GTG GTA TTC

50
Gln Thr Lys Arg Ser Lys Gln Val Cys Ala Asp Pro Ser Glu Ser
CAA ACC AAA AGA AGC AAG CAA GTC TGT GCT GAT CCC AGT GAA TCC 60                                  69
Trp Val Gln Glu Tyr Val Tyr Asp Leu Glu Leu Asn OP
TGG GTC CAG GAG TAC GTG TAT GAC CTG GAA CTG AAC TGA GCTGCTCA
    •          •          •          •          •
GAGACAGGAAGTCTTCAGGGAAGGTCACCTGAGCCCGGATGCTTCTCCATGAGACACATC
    •          •          •        +100         •         •
TCCTCCATACTCAGGACTCCTCTCCGCAGTTCCTGTCCCTTCTCTTAATTTAATCTTTTT
    •          •          •          •          •         •
TATGTGCCGTGTTATTGTATTAGGTGTCATTTCCATTATTTATATTAGTTTAGCCAAAGG
    •        +200         •          •          •         •
ATAAGTGTCCTATGGGGATGGTCCACTGTCACTGTTTCTCTGCTGTTGCAAATACATGGA
    •          •
TAACACATTTGATTCTG
```

FIG. 2

| | | |
|---|---|---|
| 1. hu-MIP-1α | 1 | MqVSTaAlaVLLCTMaLCNQ FSAslaADTPTACCFSYtSRqIPqnFIaDYFETSSgCSkPGVIFLTKRsRQ |
| 2. mu-MIP-1α | 1 | MKVSTtALaVLLCTMtLCNQvFSAPyGADTPTACCFSY SrkIPRqFIvDYFETSSLCSqPGVIFLTKRnRQ |
| 3. mu-MIP-1β | 1 | MKLCVsALsLLLLVAAFCaPgFSAPMGSDPPTsCCFSYTSRqlhRsFVmDYYETSSLCSkPAVVFLTKRgRQ |
| 4. hu-MIP-1β | 1 | MKLCVtvLSLLmLVAAFCsPalSAPMGSDPPTaCCFSYTaRkLpRnFVvDYYETSSLCSqPAVVFqTKRskQ |

| | | |
|---|---|---|
| 1. hu-MIP-1α | 72 | vCADpsEeWVQkYvsDLELsA |
| 2. mu-MIP-1α | 72 | ICADskEtWVQEYitDLELNA |
| 3. mu-MIP-1β | 73 | ICAnPSEpWVtEYmsDLELN |
| 4. hu-MIP-1β | 73 | vCAdPSEsWVqEYvyDLELN |

FIG. 3

EXPRESSION OF MACROPHAGE INDUCIBLE PROTEINS (MIPS) IN YEAST CELLS

This application is a continuation of application Ser. No. 07/951,321, filed 25 Sep. 1992, now abandoned which is a continuation of application Ser. No. 07/582,636, filed 14 Sep. 1990, now abandoned.

BACKGROUND OF THE INVENTION

Macrophage inducible proteins (MIPS) are proteins that are produced by certain mammalian cells (for example, macrophages and lymphocytes) in response to stimuli such as gram negative bacterial lipopolysaccharide and concanavalin A. Thus, the MIP molecules may have diagnostic and therapeutic utility for detecting and treating infections, cancer, myleopoietic dysfunction and auto-immune diseases.

Murine MIP-1 is a major secreted protein from lipopolysaccharide (LPS)-stimulated RAW 264.7 cells, a murine macrophage tumor cell line. It has been purified and found to consist of two related proteins MIP-1α and MIP-1β (Wolpe et al., 1987 J. Exp. Med. 167: 570; Sherry et al., 1988, J. Exp. Med. 168: 2251).

The cDNAs for both murine MIP-1α and murine MIP-1β have been cloned and sequenced (Davatelis et al., 1988, J. Exp. Med. 167:1939; Sherry et al., op. cit.) The cloning and sequencing of cDNAs corresponding to murine MIP-1α and MIP-1β have also been accomplished (Brown et al., 1989, J. Immun. 142:679; Kwon and Weissman, 1989, Proc. Natl. Acad. Sci. USA 86:1963 and by Brown al., op. cit.) Both groups isolated these homologs of MIP-1α and/or MIP-1β from cDNA libraries prepared from RNA of murine helper T-cells that had been activated by treatment with concanavalin A. These results suggest that MIP-1α and MIP-1β may play a role in T-cell activation.

Several groups have cloned what are likely to be the human homologs of MIP-1α and MIP-1B. In all cases, cDNAs were isolated from libraries prepared against activated T-cell RNA. Thus both Obaru et al., (J. Biochem. 99:885, 1986) and Zipfel et al. (J. Immun. 142:1582, 1989) have reported the cloning of a cDNA that encodes a protein with high homology to MIP-1α (76%). Similarly, Brown et al, op cit., Zipfel et al., op. cit.; Lipes et al., (Proc. Natl. Acad. USA 85:9704, 1988) and Miller, et al. (J. Immun., 143:2907, 1989) have reported the cloning and sequencing of human cDNAs, which predict a protein with high homology to MIP-1β (75%). In addition to the above described highly homologous proteins, MIP-1α and MIP-1β belong to a newly described family of related proteins which have immunomodulatory activities (see Sherry et al., op. cit. for a review).

The definition of the bioactivities of MIP-1 has begun and has utilized native MIP-1 and very recently recombinant muMIP-1α and muMIP-1β. Among the bioactivities defined for native MIP-1 is colony stimulating factor promoting activity. (Broxmeyer, et al., J. Exp. Med. 170:1583, 1989). Murine MIP-1 or murine MIP-1α but not MIP-1β have also been found to inhibit hematopoietic stem cell proliferation (Graham, et al., Nature 344:442, 1990) Due to the necessity for quantities of purified factors to pursue definition of bioactivities and the expense of isolating these factors from mammalian cell culture fluids it is desirable to produce MIP proteins by recombinant DNA technology.

MIP-1 and some members of the MIP-1 related gene family have been expressed by recombinant DNA technology as described below. Included as well is background data on members of the MIP-2 gene family, the members of which are distantly related to members of the MIP-1 gene family. Murine MIP-1α and MIP-1β have been independently expressed in COS cells (Graham, et al., op. cit.) LD78 cDNA (Obaru, et al., op. cit.) which encodes a protein that is likely to be the human homolog of murine MIP-1α has been expressed in E. coli as a carboxyl terminal fusion to human IL-2 as well as in COS cells (Yamamura, et al., J. Clin. Invest. 84:1707, 1989). Human I-309, a cDNA that encodes a protein with homology to the MIP-1 family of proteins, has been expressed in COS-1 cells in order to confirm that it encodes a secreted protein (Miller, et al., op. cit.). JE, a cDNA that encodes a protein with homology to MIP-1α and MIP-1β, has been expressed in COS-1 cells; it encodes a polypeptide core of about 12 kDa (Rollins et al., 1988, Proc. Natl. Acad. Sci. USA 85:3738).

KC, a cDNA that encodes a protein with homology to MIP-2, has been expressed in COS-1 cells to show that it encodes a secreted protein (Oguendo et al., 1989, J. Biol. Chem. 264:4133) Connective tissue activating peptide-III (CTAP, Mullenbach et al., 1986, J. Bio Chem. 261:719) and IP-10, (Luster and Ravetch, 1987, J. Exp. Med. 166:1084) both members of the MIP-2 gene family, have been expressed as an a-factor fusion in yeast and in E. coli, respectively. Maione et al., (1990, Science 247:77) expressed human platelet factor 4, (MIP-2 family) in E. coli as a protein fusion to 35 amino acids of E. coli β-glucuronidase. The insoluble fusion must be cleaved with cyanogen bromide in order to generate bioactive material. Lindley et al., (1988, Proc. Natl. Acad. Sci. USA, 85:9199) have expressed NAF (IL-8), a member of the MIP-2 family, in E. coli. After purification and renaturation, this recombinant protein was found to have the same bioactivity identified for the native molecule. Furuta et al., (1989, J. Biochem. 106:436) have also expressed IL-8 (MDNCF) in E. coli. Lipes, et al. (op. cit.) described baculovirus expression of Act-2 cDNA, which encodes human MIP-1β. Finally, Gimbrone et al., (1989 Science 246:1601) have expressed endothelial IL-8 in human 293 cells and have shown that the recombinant and natural material have the same bioactivity. However, MIP-1α and MIP-1β have yet to be expressed in yeast cells.

Thus, there is a need in the art for additional sources of mammalian inflammation mediator proteins to provide an economical way to obtain useful amounts of the proteins.

SUMMARY OF THE INVENTION

It is an object of the invention to provide a DNA molecule which is active as a template for producing mammalian macrophage inflammatory proteins (MIPS) in yeast.

It is another object of the invention to provide a yeast cell containing a DNA molecule which is active as a template for producing mammalian macrophage inflammatory proteins.

It is yet another object of the invention to provide a method of producing MIP-1 polypeptides.

It is still another object of the invention to provide MIP-1 compositions.

These and other objects of the invention are provided by one or more of the embodiments described below. In one embodiment, a DNA molecule is provided which comprises, in order of transcription: (a) a transcription regulatory region operative in a yeast; (b) a region which encodes a mammalian protein selected from the group consisting of MIP-1α, and MIP-1β; said molecule active as a template for producing the mammalian protein in yeast.

In another embodiment of the invention a yeast cell is provided which contains a DNA molecule comprising, in order of transcription: (a) a transcription regulatory region operative in a yeast; (b) a region which encodes a mammalian protein selected from the group consisting of MIP-1α, and MIP-1β; said molecule active as a template for producing the mammalian protein in yeast.

In still another embodiment of the invention a method is provided for producing a MIP polypeptide which comprises: growing a yeast cell in a nutrient medium whereby a MIP is expressed, said cell having a DNA molecule comprising in order of transcription: (a) a transcription regulatory region operative in a yeast; (b) a region which encodes a mammalian protein selected from the group consisting of MIP-1α, and MIP-1β; said molecule active as a template for producing the mammalian protein in yeast.

In still another embodiment of the invention a composition is provided which comprises a mammalian protein selected from the group consisting of murine MIP-1α, murine MIP-1β, human MIP-1α and human MIP-1β, wherein the MIP is substantially free of non-MIP, mammalian proteins, and wherein the MIP is synthesized in a yeast cell.

The present invention thus provides the art with economical means to produce mammalian MIP proteins in ample quantities. This allows the full range of their bioactivities to be determined, and allows their use diagnostically and therapeutically.

BRIEF DESCRIPTION OF THE FIGURES

FIG. 1 displays the cDNA sequence and predicted protein sequence of human MIP-1α.

FIG. 2 displays the CDNA sequence and predicted protein sequence of human MIP-1β.

FIG. 3 shows an alignment of the predicted amino acid sequences of MIP-1 homologs.

DETAILED DESCRIPTION OF THE INVENTION

It is a finding of the present invention that the mammalian MIP proteins can be expressed in and secreted from yeast cells. The proteins so expressed have biological activity. Thus yeast cells transformed with appropriate DNA constructs are suitable sources of MIP for therapeutic and investigational purposes.

MIP-1 is a monokine which acts as a primary negative regulator of hematopoietic stem cell proliferation. For example, MIP-1 is known to inhibit DNA synthesis in primative hematopoietic cells (CFU-A) (Graham, et al., op. cit.). In addition, it enhances proliferation of more mature hematopoietic cells, including CFU-GM (Broxmeyer, et al., op. cit.) which have been stimulated with GM-CSF.

According to the findings of the present invention DNA molecules and host cells are provided for making MIP-1 proteins in yeast. The DNA molecules contain a region which encodes at least one mammalian MIP-1 protein. The MIP-1 may be human or murine, for example, and may consist of either the α or the β subunit. The MIP-1 coding region may also encode related proteins such as "muteins." These are closely related proteins which have been altered slightly to change one or more amino acids of the sequence, for example by substitution, deletion or insertion. Preferably less than about 8 amino acids have been altered, ususally 4 or less, and more typically 2 or less. It may be preferred to make conservative substitutions, i.e., exchanging one amino acid for another of similar properties, such as charge. Muteins typically retain all of the activity of the parent protein, but may have increased stability or other useful properties relative to the natural protein. The MIP-1 coding region may also encode a truncated MIP-1. Typically the truncated protein retains activity or unique epitopes of MIP-1.

The coding region is linked to a transcription regulatory region which is operative in a yeast. The transcription regulatory region may provide inducible or constitutive expression, as is desired. At a minimum, the regulatory region provides a promoter for initiation of transcription by RNA polymerase. The regulatory region may be derived from any yeast gene having the desired regulatory properties. For example, the yeast alcohol dehydrogenase, hexokinase, enolase, glyceraldehyde-3-phosphate dehydrogenase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase promoters can be used. These promoters are well known in the art. The transcription regulatory region is linked to the coding region such that transcription from the regulatory region continues through the coding region. When the DNA molecule of the invention is present in a yeast cell, MIP messenger RNA is made and translated. Expression according to the present invention denotes transcription and translation of a DNA sequence to produce a MIP protein.

A yeast promoter is any DNA sequence capable of binding yeast RNA polymerase and initiating the downstream (3') transcription of a coding sequence (e.g., structural gene) into mRNA. A promoter will have a transcription initiation region which is usually placed proximal to the 5' end of the coding sequence. This transcription initiation region typically includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (E.P.O. Pub. No. 284044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (E.P.O. Pub. No. 329203). The yeast PHO5 gene, encoding acid phosphatase, also provides useful promoter sequences [Miyanohara, et al., (1983) *Proc. Natl. Acad. Sci. USA* 80:1].

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197; 4,880,734). Other examples of hybrid promoters include promoters which consist of the regulatory sequences of either the ADH2, GAL4, GAL10, or PHO5 genes, combined with the transcriptional activation region of a glycolytic enzyme gene such as GAP or PyK (E.P.O. Pub. No. 164556). Furthermore, a yeast promoter can include naturally occurring promoters of non-yeast origin that have the ability to bind yeast RNA polymerase and initiate transcription. See, e.g., Cohen, et al. (1980) *Proc. Natl. Acad. Sci. USA* 77:1078; Henikoff, et al. (1981) Nature, 283:835; Hollenberg, et al., (1981) *Curr. Topics Microbiol.*

*Immunol.* 96:119, Hollenberg, et al., "The Expression of Bacterial Antibiotic Resistance Genes in the Yeast *Saccharomyces cerevisiae*," in: *Plasmids of Medical, Environmental and Commercial Importance* (eds. K. N. Timmis and A. Puhler); Mercereau-Puigalon, et al. (1980) Gene 11:163; Panthier, et al. (1980) Curr. Genet., 2:109.

A promoter sequence may be directly linked with the DNA molecule encoding MIP, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative to direct expression. Typically, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See, e.g., EPO Pub. No. 196056. Another example is a ubiquitin fusion protein. Such a fusion protein is made with the ubiquitin "leader" or "pro-" region that preferably retains a site for a processing enzyme (e.g. ubiquitin-specific processing protease) to cleave the ubiquitin from the foreign protein. Through this method, therefore, native foreign protein can be isolated (PCT WO 88/024066; commonly owned U.S. patent application Ser. No. 390,599, filed 7 Aug. 1989, the disclosure of which is incorporated herein by reference).

Alternatively, foreign proteins can also be secreted from the cell into the growth media by creating chimeric DNA molecules that encode a fusion protein comprised of a leader sequence fragment that provide for secretion in yeast and the foreign gene. Preferably, there are processing sites (in vivo or in vitro) encoded between the leader fragment and the foreign gene. Preferred in vivo sites include dibasic sequences such as lys-lys, arg-arg, lys-arg, and arg-lys. The leader sequence fragment typically encodes a signal peptide comprised of hydrophobic amino acids which direct the secretion of the protein from the cell. DNA encoding suitable signal sequences can be derived from genes for secreted yeast proteins, such as the yeast invertase gene (E.P.O. Pub. No. 12,873; J.P.O. Pub. No. 62,096,086) and the A-factor gene (U.S. Pat. No. 4,588,684). Alternatively, leaders of non-yeast origin, such as an interferon leader, exist that also provide for secretion in yeast (U.S. Pat. No. 4,775,622). Concomitant cleavage of the signal peptide from the MIP is also desirable. This is usually accomplished at a processing site. The processing is preferably accomplished in vivo by endogenous yeast enzymes during the process of translocation. Alternatively, in vitro processing can be employed using non-yeast enzymes or chemical cleavage.

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (typically about 25 to about 50 amino acid residues) (U.S. Pat. Nos. 4,546,082 and 4,870,008; E.P.O. Pub. No. 324274). Additional leaders employing an alpha-factor leader fragment that provides for secretion include hybrid alpha-factor leaders made with a presequence of a first yeast, but a pro-region from a second yeast alpha-factor. (See, e.g., PCT WO 89/02463.)

The DNA molecules of the present invention will typically contain termination signals for transcription at the 3' end of the MIP protein coding region. This signal can be from any yeast gene, such as those used to supply promoters or signal sequences. In addition, the DNA molecules will typically contain a replication origin so that the DNA molecule can function as an autonomous unit for DNA replication. Often the DNA molecule will be in the form of a plasmid, although cosmids, viruses and mini-chromosomes can also be used. Often, the DNA molecule will be bifunctional, i.e., able to maintain itself in cells of two different genera.

Examples of yeast-bacteria shuttle vectors include YEp24 [Botstein, et al., (1979) *Gene*, 8:17–24], pCl/1 [Brake, et al., (1984) *Proc. Natl. Acad. Sci. USA*, 81:4642–4646], and YRp17 [Stinchcomb, et al., (1982) *J. Mol. Biol.*, 158:157]. In addition, a replicon may be either a high or low copy number plasmid. A high copy number plasmid will generally have a copy number ranging from about 5 to about 200, and typically about 10 to about 150. A host containing a high copy number plasmid will preferably have at least about 10, and more preferably at least about 20. Either a high or low copy number vector may be selected, depending upon the effect of the vector and the foreign protein on the host. See, e.g., Brake, et al., supra.

Alternatively, the expression constructs can be integrated into the yeast genome with an integrating vector. Integrating vectors typically contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver, et al. (1983), *Methods in Enzymol.*, 101:228–245]. An integrating vector may be directed to a specific locus in yeast by selecting the appropriate homologous sequence for inclusion in the vector. See Orr-Weaver, et al., supra. One or more expression constructs may integrate, possibly affecting levels of recombinant protein produced [Rine, et al., (1983) *Proc. Natl. Acad. Sci., USA* 80:6750]. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Typically, extrachromosomal and integrating expression constructs may contain selectable markers to allow for the selection of yeast strains that have been transformed. Selectable markers may include biosynthetic genes such as ADE2, HIS4, LEU2, TRP1, and URA3. Selectable markers may also include drug resistance genes such as ALG7 or a G418 resistance gene, which confer resistance in yeast cells to tunicamycin and G418, respectively. In addition, a suitable selectable marker may also provide yeast with the ability to grow in the presence of toxic substances, such as certain metals. For example, the presence of CUP1 allows yeast to grow in the presence of copper ions [Butt et al. (1987) *Microbiol. Rev.* 51:351].

Expression vectors, either extrachromosomal replicons or integrating vectors, have been developed for transformation into many yeasts. For example, expression vectors have been developed for inter alia, the following yeasts: *Candida albicans* [Kurtz, et al. (1986) *Mol. Cell. Biol.*, 6:142], *Candida maltosa* [Kunze, et al. (1985), *J. Basic Microbiol.*, 25:141], *Hansenula polymorpha* [GleesoN, et al., (1986) *J. Gen. Microbiol.*, 132:3459; Roggenkamp, et al. (1986), *Mol.*

*Gen. Genet.,* 202:302], *Kluyveromyces fragilis* [Das, et al., (1984), *J. Bacteriol.,* 158:1165], *Kluvveromycces lactis* [De Louvencourt et al., (1983), *J. Bacteriol.,* 154:737; Van den Berg, et al., (1990) *Bio/Technology,* 8:135], *Pichia guillerimondii* [Kunze et al., (1985), *J. Basic Microbiol.,* 25:141], *Pichia pastoris* [Cregg, et al., (1985), *Mol. Cell Biol.,* 5:3376; U.S. Pat. Nos. 4,837,148, 4,879,231, and 4,929, 555], *Saccharomyces cerevisiae* [Hinnen et al., (1978), *Proc. Natl. Acad. Sci. USA,* 75:1929; Ito, et al., (1983) *J. Bacteriol.,* 153:163], *Schizosaccharomyces pombe* [Beach and Nurse (1981), *Nature,* 300:706], and *Yarrowia lipolytica* [Davidow, et al., (1985), *Curr. Genet.,* 10:39–48; Gaillardin, et al. (1985), *Curr. Genet.,* 10:49].

In general, DNA encoding a mammalian MIP may be obtained from human, murine, or other sources by constructing a cDNA library from mRNA isolated from mammalian tissue, and screening with labeled DNA probes encoding portions of the human or murine chains in order to detect clones in the CDNA library that contain homologous sequences. Alternatively, polymerase chain reaction (PCR) amplification of the cDNA (from mRNA) and subcloning and screening with labeled DNA probes may be used. Clones may be analyzed by restriction enzyme analysis and nucleic acid sequencing so as to identify full-length clones. If full-length clones are not present in the library, fragments can be recovered from the various clones and ligated at restriction sites common to the clones to assemble a clone encoding a full-length molecule. Any sequences missing from the 5' end of the cDNA may be obtained by the 3' extension of synthetic oligonucleotides complementary to MIP sequences using mRNA as a template (the primer extension technique.) Alternatively, homologous sequences may be supplied from known cDNAs derived from human or murine sequences disclosed herein.

The practice of the present invention will employ unless otherwise indicated, conventional molecular biological, microbiological and recombinant DNA techniques, all within the skill of the ordinary artisan. Such techniques are set forth in the literature. See, e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. 1985); "Transcription and Translation" (B. D. Hames & S. J. Higgins eds. 1984); "Animal Cell Culture" (R. I. Freshney ed. 1986); "Immobilized Cells and Enzymes": (IRL Press, 1986); B. Perbal, "A Practical Guide to Molecular Cloning" (1984).

As used herein, "yeast" includes ascosporogenous yeasts (Endomyceltales), basidiosporogenous yeasts and yeast belonging to the Fungi imperfecti (Blastomycetes). The ascosporogenous yeasts are divided into two families. Spermophthoraceae and Saccharomycetaceae. The latter is comprised of four subfamilies, Schizosaccharomycoidaea (e.g., genus Schizosccharomyces), Nadsonioideae, Lipomycoideae and Saccharomycoideae (e.g., genera Pichia, Kluyveromyces and Saccharomyces). The basidiosporogenous yeasts include the genera Leucosporidium, Rhodosporidium, Sporidiobolus, Filobasidium and Filobasidiella. Yeast belonging to the Fungi Imperfecti are divided into two families, Sporobolomycetaceae (e.g., genera Sporobolomyces, Bullera) and Cryptococcaceae (e.g., genus Candida). Of particular interest to the present invention are species within the genera Pichia, Kluyveromyces, Saccharomyces, Schizosaccharomyces and Candida. Of particular interest are the Saccharomyces species *S. cerevisiae, S. carlsbergensis, S. diastaticus, S. douglasii, S. kluvveri, S. norbensis* and *S. oviformis*. Species of particular interest in the genus Kluyveromyces include *K. lactis*. Since the classification of yeast may change in the future, for the purposes of this invention, yeast shall be defined as described in *Biology and Activities of Yeast* (F. A. Skinner, S. M. Passmore & R. Davenport eds. 1980) (Soc. App. Bacterial. Symp. Series No. 9). In addition to the foregoing, those of ordinary skill in the art are presumably familiar with the biology of yeast and the manipulation of yeast genetics. See, e.g., *Biochemistry and Genetics of Yeast* (M. Bacila, B. L. Horecker & A.O.M. Stoppani eds. 1978); *The Yeasts* (A. H. Rose & J. S. Harrison eds., 2nd ed., 1987); *The Molecular Biology of the Yeast Saccharomyces* (Strathern et al., eds. 1981). The disclosures of the foregoing references are incorporated herein by reference.

Yeast cells are transformed with the DNA molecules of the present invention according to known techniques for introduction of DNA. (See, e.g., Hinnen et al. (1978) PNAS 75:1919–1933 and Stinchcomb et. al. EP 45,523.) Methods of introducing exogenous DNA into yeast hosts are well-known in the art, and typically include either the transformation of spheroplasts or of intact yeast cells treated with alkali cations. Transformation procedures usually vary with the yeast species to be transformed. See, e.g., Kurtz, et al. (1986), *Mol. Cell. Biol.,* 6:142, Kunze, et al. (1985), *J. Basic Microbiol.,* 25:141, for *Candida;* Gleeson, et al., (1986), *J. Gen. Microbiol.,* 132:3459, Roggenkamp, et al. (1986), *Mol. Gen. Genet.,* 202:302, for *Hansenula;* Das, et al., (1984), *J. Bacteriol.,* 158:1165, De Louvencourt et al., (1983), *J. Bacteriol.,* 154:1165, Van den Berg, et al., (1990), *Bio/Technology,* 8:135, for *Kluyveromyces;* Cregg, et al., (1985), *Mol. Cell Biol.,* 5:3376, Kunze, et al. (1985), *J. Basic Microbiol.,* 25:141, U.S. Pat. Nos. 4,837,148 and 4,929,555, for Pichia; Hinnen, et al. (1978), *Proc. Natl. Acad. Sci. USA,* 75:1929, Ito, et al. (1983), *J Bacteriol.,* 153:163, for *Saccharomyces;* Davidow, et al., (1985) *Curr. Genet.,* 10:39, Gaillardin, et al. (1985), *Curr. Genet.,* 10:49, for *Yarrowia*.

Yeast cells are grown in culture in nutrient media according to well known techniques. (See, e.g., American Type Culture Collection Media Handbook.) According to the present invention yeast cells which "have" a certain DNA molecule contain that molecule stably, that is, the DNA is faithfully replicated in the cells. A single yeast cell, according to the invention can be transformed with DNA for either/or both of the MIP-1 subunits α and βB. Thus monomer, homomers and heteromers could be formed in the yeast or in the culture medium.

The practice of the teachings of the present invention leads to compositions containing mammalian MIP-1 proteins. These compositions are substantially free of non-MIP, mammalian proteins, because they are produced in yeast cells. "Substantially free" denotes greater than about 75% by weight MIP relative to the protein content of the entire composition. Preferably, the MIP is greater than about 90% by weight, and most preferably the MIP is greater than about 99% by weight of the protein of the composition. Indeed, compositions in which the only mammalian protein is an MIP-1 are provided by the present invention.

The following examples are provided for illustrative purposes and do not limit the scope of the invention.

EXAMPLES

Example 1

This example describes the cloning of murine MIP-1α and murine MIP-1β coding sequences.

A cDNA library was constructed from Poly(A)+ RNA isolated from E. coli lipopolysaccharide-stimulated RAW 264.7 (murine macrophage tumor cell line) cells. The cloning of the cDNAs for murine MIP-1α and murine MIP-1β are described in Davatelis et al., J. Exp. Med. 167, 1939–1944 (1988), and Sherry et al., J. Exp. Med. 168, 2251–2259 (1988), which are incorporated by reference herein.

Example 2

This example describes the cloning of human MIP-1α and human MIP-1β coding sequences.

1. Library Construction

The human monocytic-like cell line U937 was grown to confluence and stimulated to differentiate by the addition of phorbol 12-myristate 13-acetate (PMA) to a final concentration of $5 \times 10^{-8}$M. After 24 hours in the presence of PMA, lipoplysaccharide was added to a final concentration of 1 μg/ml and the cells were incubated for an additional 3 hours at 37° C. Total RNA was prepared essentially as described by Cathala et al., (DNA 2: 329, 1983). Poly A+ RNA was prepared by a single passage over oligo-dT cellulose, essentially as described by Okayama et al. (Methods Enzymol. 154, 3, 1987) and Maniatis et al., (Molecular Cloning: A Laboratory manual, Cold Spring Harbor Laboratory, 1982). Double-stranded cDNA was prepared by standard methods and cloned and packaged into λgt10. Duplicate nitrocellulose filter lifts of the plated library ($5.6–7 \times 10^5$ plaques) were pre-hybridized at 52° C. in 50% formamide, 5xSSC, 50 mM sodium phosphate buffer, pH6.5, 0.2% SDS, 2x Denhardt's and 0.25 mg/ml sonicated salmon sperm DNA. Filters were then hybridized at 42° C. overnight in 50% formamide, 5xSSC, 20 mM sodium phosphate, pH6.5, 0.1% SDS, 1xDenhardt's, 10% dextran sulfate, 0.1 mg/ml sonicated salmon sperm DNA and approximately 500,000 cpm per ml of the appropriate $^{32}$P-ATP nick-translated murine CDNA probe. 2. Screening for Human Humologs to mu-MIP-1α, mu-MIP-1β

In order to screen for human homologs to murine MIP-1α and MIP-1β, the following two fragments were isolated. For MIP-1α, a 236 bp KpnI-SalI fragment was isolated from pMIP200. (Construction of pMIP200 is described below.) This fragment includes all of the murine MIP-1α mature coding sequence. To screen for homologs to murine MIP-1β, a 213 bp NcoI-SalI fragment was isolated from pMIP300. (Construction of pMIP300, is described below.) This fragment encodes all but the first two amino acids of the murine MIP-1I mature coding sequence.

The DNA fragments were nick translated and 500,000 cpm per ml of each nick translated probe was hybridized to the U937 cDNA library. Both probes were included in the first round of screening. Filters were subjected to three low stringency washes for 30 minutes each at room temperature in 2xSSC, 0.1% SDS.

Many positive clones were identified. Nineteen were chosen for a second round of plaque purification. Duplicate filter lifts from these plates were independently hybridized, as described above, with either the murine MIP-1α or the murine MIP-1β cDNA probe. Washes were as for the primary screening. This screening showed that under these wash conditions it was not possible to distinguish between clones homologous to murine MIP-1α and MIP-1β.

3. Determining the Sequence of Human MIPs

The nucleotide sequence from nine independent phage clones was determined by the dideoxy chain termination method of Sanger et al., (Proc. Natl. Acad. Sci. USA 74, 5463 (1977), following subcloning of insert DNA into the M13 phage vector. Two cDNA homologs were defined. Based on nucleotide sequence homology to the two murine MIP-1 peptides, clones MIP-1 2b, 3a, 4a, 4b and 5b defined the human homolog of mu-MIP-1α, CDNA hu-MIP-1α (FIG. 1); and clones MIP1–8a, 11b, 13a defined the human homolog to mu-MIP-1β, cDNA hu-MIP-1β (FIG. 2). Assignment of cDNAs as human homologs of murine MIP-1α or -1β was based on both nucleotide and amino acid homology comparisons. Hu-MIP-1α has 68.5% (740 nucleotide overlap) homology to mu-MIP-1α and 57.8% nucleotide homology (555 nt overlap) to mu-MIP-1β. The percentage nucleotide identity of hu-MIP-1β to mu-MIP-1α and mu-MIP-1β is 59.0% (559 nt overlap) and 72.7% (600 nt overlap) respectively. The percent identity of the predicted protein sequence of hu-MIP-1α to that of mu-MIP-1α and mu-MIP-1β is 75.3% (93 aa overlap) and 58.2% (91 aa overlap) respectively. Similarly hu-MIP-1β has 59.3% (91 aa overlap) and 74.7% (91 aa overlap) amino acid sequence identity to mu-MIP-1α and mu-MIP-18, respectively. An alignment of the predicted amino acid sequences of these MIP-1 homologs is presented in FIG. 3.

Hu-MIP-1α cDNA is identical to cDNAs LD78 and AT464 isolated previously by Obaru et al., op. cit., and Zipfel et al., op. cit. respectively. Hu-MIP-1β cDNA is virtually identical to cDNAs isolated by Brown et al., op. cit. Zipfel et al., op. cit., Lipes et al., op. cit. and Miller, et al., op. cit. All of these proteins are members of a newly described family of related proteins which appear to function in the host response to invasion. (See Sherry et al., J. Exp. Med. 168: 2251, 1988, for a review.)

Example 3

This example describes the construction of MIP expression plasmids.

a. pYMIP200 (murine MIP-1α)

This plasmid encodes an alpha factor leader linked to the sequence encoding mature murine MIP-la. The MIP-1α mature coding sequence is derived from the corresponding MIP-1α cDNA (Davatelis et al. (1988) J. Exp. Med. 167 1939–1943). The GAPDH promoter sequence, the alpha factor leader sequence and the alpha factor transcription terminator are derived from plasmid pGAI1, the construction of which is described in European patent application 0 324 274, entitled, "Improved expression and secretion and heterologous proteins in yeast employing truncated alpha-factor leader sequences," the disclosure of which is expressly incorporated by reference herein.

Construction of pYMIP-200 was accomplished as follows. Plasmid pBR322/NAP850 which contains a cDNA encoding MIP-1α cloned in the EcoR1 site of pBR322 was digested with NdeI and BsmI and the 196 bp fragment encoding all but the first two N-terminal amino acids of the mature MIP-1α sequence was ligated with the following adaptors:

```
a)  KpnI-NdeI adaptor
    5'              CCTTGGATAAAAGAGCGCCA        3'
    3'        CATGGGAACCTATTTTCTCGCGGTAT        5'
b)  BsmI → SalI adaptor
    5'                  TGATAGCGTCG             3'
    3'                GGACTATCGCAGCAGCT         5'
                      ↓ A (silent mutation, see below)
```

The resulting fragment was purified on an acrylamide gel. This fragment was then ligated into PGAI1 that had been digested with KpnI and SalI and purified on an agarose gel.

Following bacterial transformation and screening, plasmid pMIP200 was obtained. Upon DNA sequencing it was found to have a silent mutation in the nucleotide sequence coding for the C-terminal alanine (GCC→GCT). The BamHI expression cassette from this plasmid was cloned into the BamHI site of shuttle vector pAB24 (see European Patent Application 0 324 274 A1) to generate pYMIP200. pAB24 contains the complete 2μ sequence (Broach in: Molecular Biology of the Yeast Saccharomyces, vol. 1, p. 455 (1981).)

b. pYMIP300 (murine MIP-1β)

This plasmid encodes an alpha factor leader linked to the sequence encoding mature murine MIP-1β. The sequence encoding MIP-1α is derived from the MIP-1β cDNA (Sherry et al. (1988) J. Exp. Med. 168, 2251–2259). The GAPDH promoter sequence, the alpha factor leader sequence and the alpha factor transcription terminator are derived from plasmid pGAI1 which is described above. The cDNA encoding MIP-1β was subjected to in vitro mutagenesis to introduce a restriction endonuclease site which would facilitate the cloning of the MIP-1β coding region into the expression vector. The mutagenic primer used was:

3' GTC CCA AGA GGC GGG GGT ACC CGA GAC -5'

(* refers to nucleotides that are different from those in the cDNA sequence)

This primer introduced a NcoI site at the start of the nucleotide sequence encoding the mature MIP-1β protein. The EcoRI fragment containing the modified MIP-1β CDNA sequence (containing the NcoI site) was isolated from the M13 phage RF and cloned into the EcoRI site of pBR322 to give plasmid pBR-3-lb/6. This plasmid was cut with BglII and ligated to the following BglII-SalI adaptor which encodes the 20 carboxyl terminal amino acids of MIP-1β and the stop codon.

Ile Cys Ala Asn Pro Ser Glu Pro Trp Val Thr Glu Tyr Met Ser Asp Leu Glu Leu Asn OP AM Arg Arg Arg
GATCTGTGCTAACCCCAGTGAGCCCTGGGTCACTGAGTACATGAGCGATCTAGAGCTGAACTGATAGCGTCG
    ACACGATTGGGGTCACTCGGGACCCAGTGACTCATGTACTCGCTAGATCTCGACTTGACTATCGCAGCAGCT

1 BGL2,   50 XBAI                                                          73 SALI,

Following digestion with NcoI, a 213 bp fragment encoding MIP-1β and stop codons was purified by acrylamide gel electrophoresis.

5'- CCTTGGATAAAAGAGCCCC -3'
3'- CATGGGAACCTATTTTCTCGGGGGTAC -5'

The vector was then cut with SalI, and the vector fragment purified by agarose gel electrophoresis. The NcoI-SalI vector fragment was ligated with the NcoI-SalI MIP-1β coding fragment. The ligated product was transformed into E. coli and the clone pMIP300/20 was obtained which was found to have the predicted nucleotide sequence. This plasmid was digested with BamHI and the resulting 1155 bp fragment including the GAPDH promoter sequence, the sequence encoding the alpha factor leader-MIP-1 fusion protein and the alpha factor transcription terminator was cloned into the BamHI site of pAB24 to give the expression plasmid pYMIP300.

c. pYMIP220 (human MIP-1α)

This plasmid encodes an alpha factor leader linked to the sequence encoding mature hu-MIP-1a. The hu-MIP-1α sequence is derived from the λgt10 CDNA clone hMIP1–13a. The GAPDH promoter sequence, the alpha factor leader sequence and the alpha factor transcription terminator are derived from plasmid pGAI1, the construction of which is described in European patent application 0324-274. The EcoR1 insert DNA fragment from a λgt10 clone of human MIP-1 was subjected to 30 cycles of polymerase chain reaction (PCR) with the following primers.

5'- primer

5' GAGTGCGGTACCCTTGGATAAAAGAGCATCACTTGCTGCTGACACGCCGACCGC -3'
          ↑                              | →hu-MIP-1α
         KpnI

3'- primer

5' GAGTGCGTCGACTCATCAGGCACTCAGCTCCAGGTCGCTGAC -3'
       ↑         - -       | ←hu-MIP-1α
      SalI      stop The vector PGAI1 was cut with KpnI and ligated with the following KpnI-NcoI adaptor which encodes the 3 carboxyl terminal amino acids of the alpha factor leader, the LysArg processing site and the first two amino acids of mature MIP-1β.

The amplified DNA was digested with KpnI and SalI and the 235 bp fragment encoding the 4 carboxyl terminal amino acids of the alpha factor leader, the dibasic processing site, and the entire 70 amino acids of mature hu-MIP-1α was isolated by acrylamide gel electrophoresis. This fragment was then ligated into pGAI1 that had been digested with KpnI and SalI and purified on an agarose gel. Following bacterial transformation and screening, plasmid pMIP220 was obtained which upon DNA sequencing was found to have the predicted nucleotide sequence. This plasmid was digested with BamHI and the resulting 1154 bp fragment including the GAPDH promoter sequence, the sequence encoding the alpha-factor leader/hu-MIP-1α fusion protein and the alpha factor transcription terminator was cloned into the BamHI site of pAB24 to give expression plasmid pYMIP220.

d. PYMIP320

This plasmid encodes an alpha factor leader linked to the nucleotide sequence encoding mature hu-MIP-1β. The mature hu-MIP-1β coding sequence is derived from a λgt10 cDNA clone of human MIP-1β. The GAPDH promoter sequence, the alpha factor leader sequence and the alpha factor transcription terminator are derived from plasmid pGAI1, the construction of which is described in European patent application 0 324 274. The EcoRI insert DNA fragment from the λgt10 clone containing the hu-MIP-1β cDNA was subjected to 30 cycles of polymerase chain reaction (PCR) with the following primers.

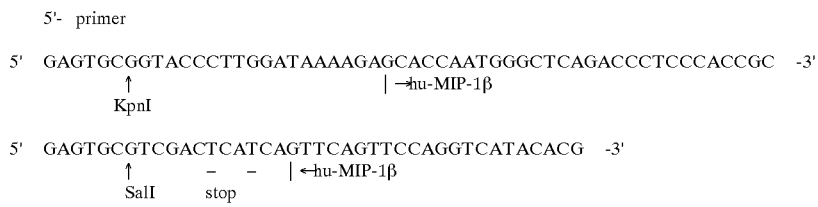

The amplified DNA was digested with KpnI and SalI and the 232 bp fragment encoding the 4 carboxyl terminal amino acids of the alpha factor leader, the dibasic processing site, the entire 69 amino acids of mature hu-MIP-1β was isolated by acrylamide gel electrophoresis. This fragment was then ligated into pGAI1 that had been digested with KpnI and SalI and purified on an agarose gel. Following bacterial transformation and screening, plasmid pMIP320 was obtained which upon DNA sequencing was found to have the predicted nucleotide sequence. This plasmid was digested with BamHI and the resulting 1143 bp fragment including the GAPDH promoter sequence, the sequence encoding the alpha factor leader/hu-MIP-1β fusion protein and the alpha factor transcription terminator was cloned into the BamHI site of pAB24 to give expression plasmid pYMIP320.

Example 4

This example demonstrates the expression of murine MIP-1α and -1β and human MIP-1α and 1-β.

Expression of MIP-1α

*S. cerevisiae* strain MB2-1 (leu2–3, leu2–112, his3–11, his3–15 ura3Δ, pep4Δ, CAN, cir°) was transformed with plasmid pYMIP200 or pYMIP220 by standard procedures and transformants selected for uracil prototrophy. Expression was analyzed by inoculation of single colonies of individual transformants into leucine selective medium and growing at 30° C. for ~48 hr. or until the culture is saturated. Cultures were then centrifuged, cells resuspended in medium lacking uracil and diluted 20-fold into uracil selective medium. Cultures were grown for approximately 72 h, then harvested and cell-free supernatants prepared.

| Recipes | |
| --- | --- |
| Leu-Selective Media | |
| 59 ml | 10X basal salts |
| 25 ml | 20X leu-supplements |
| 2 ml | 5% threonine |
| 80 ml | 50% glucose |
| 5 ml | 0.3% of each pantothenic acid and inositol |
| qs to 500 ml with sterile ddH$_2$O and then autoclave or sterile filter. | |
| 20X supplements | |
| 0.5 g powdered leu-supplements per 100 ml of sterile ddH$_2$O. Autoclave. | |
| Powdered Leu-Supplements | |
| 0.8 g | Adenine |
| 0.6 g | Uridine |
| 0.4 g | L-Tryptophan |
| 0.4 g | L-Histidine |
| 0.4 g | L-Arginine |
| 0.4 g | L-Methionine |
| 0.6 g | L-Tyrosine |

-continued

| Recipes | |
| --- | --- |
| 0.6 g | L-Lysine |
| 0.96 g | L-Phenylalanine |
| Add all components to a coffee grinder and grind until the powder is homogenous. | |
| Ura-Selective media | |
| 500 ml | 2% glucose media |
| 50 ml | 10X basal salts |
| 20 ml | 50% glucose |
| 12.5 ml | 20% casamino acids |
| 2.5 ml | 1% adenine |
| 2.5 ml | 1% tryptophan |
| 5 ml | 0.3% of each pantothenic acid and inositol |

Conditioned medium was analyzed for the presence of MIP-1α by SDS-PAGE followed by coomassie staining and, in the case of the murine factor, by immunoblotting. A band was observed on SDS-PAGE of murine MIP-1α which comigrated with native MIP-1 standard (provided by B. Sherry, Rockefeller University) and showed immunoreactivity with polyclonal antisera raised against murine MIP-1 (antisera provided by B. Sherry). A similar sized stained band was observed upon expression of human MIP-1α. These proteins were expressed as 1–5% of the secreted protein.

Expression of MIP-1β

*S. cerevisiae* strain MB2-1 was transformed with plasmid pYMIP300 or pYMIP320 by standard procedures and transformants selected for uracil prototrophy. Expression studies were performed as described above for MIP-1β. Similar results were obtained for expression levels.

Thus far, recombinant murine MIP-1α and MIP-1β have been shown to have bioactivity of native MIP-1, i.e., CSF-dependent myelopoietic enhancing activity for CFU-GM.

Table of Deposited Cell Lines

| Name | Deposit Date | ATCC No. |
|---|---|---|
| MB2-1(pYMIP-200) | June 20, 1990 | 74008 |
| MB2-1(pYMIP-220) | June 20, 1990 | 74007 |
| MB2-1(pYMIP-300) | June 20, 1990 | 74006 |
| MB2-1(pYMIP-320) | June 20, 1990 | 74005 |

The above materials have been deposited with the American Type Culture Collection, 12301 Parklawn Drive, Rockville, Md. 20852 under the accession numbers indicated. These deposits will be maintained under the terms of the Budapest Treaty on the International Recognition of the Deposit of Micro-organisms for purposes of Patent Procedure. These deposits are provided merely as convenience to those of skill in the art, and are not an admission that a deposit is required under 35 U.S.C. Section 112. The sequence of the polynucleotides contained in the deposited materials, as well as the amino acid sequence of the polypeptides encoded thereby, are incorporated herein by reference and are controlling in the event of any conflict with the description of sequences herein. A license may be required to make, use or sell the deposited materials, and no such license is hereby granted.

We claim:

1. A yeast cell producing a biologically active MIP polypeptide, said yeast cell comprising a DNA molecule comprising in order of transcription:
   (a) a transcription regulatory region operative in a yeast; and
   (b) a region which comprises a sequence that encodes a mammalian protein selected from the group consisting of MIP-1α and MIP-1β.

2. A method for producing a biologically active MIP polypeptide which comprises:
   growing a yeast cell according to claim 1 in a nutrient medium whereby region (b) is expressed to produce a biologically active MIP.

3. A yeast cell comprising a DNA molecule according to claim 1, wherein said DNA molecule further comprises a replication system operative in a yeast.

4. A method for producing a MIP polypeptide which comprises:
   growing a yeast cell according to claim 3 in a nutrient medium whereby region (b) is expressed to produce a MIP.

5. A yeast cell comprising a DNA molecule according to claim 1, wherein said DNA molecule further comprises a leader fragment which facilitates secretion of the mammalian protein, said fragment covalently linked to the 5' end of region (b).

6. A method for producing a MIP polypeptide which comprises:
   growing a yeast cell according to claim 5 in a nutrient medium whereby region (b) is expressed and secreted to produce a MIP.

7. The method of claim 6 wherein the leader fragment comprises a yeast alpha-factor leader and processing signal.

8. The method of claim 6 wherein the leader fragment comprises a truncated yeast alpha-factor leader.

9. A DNA molecule comprising in order of transcription:
   (a) a transcription regulatory region operative in a yeast;
   (b) a yeast alpha-factor leader sequence fragment;
   (c) a region which encodes a mammalian protein selected from the group consisting of murine MIP-1α, murine MIP-1β, human MIP-1α and human MIP-1β; and
   (d) a yeast alpha-factor transcription terminator.

10. A yeast cell containing the DNA molecule of claim 9.

11. A method of producing a biologically active MIP polypeptide which comprises:
   growing the yeast cell of claim 10 in a nutrient medium whereby region (c) is expressed and secreted to produce a biologically active MIP and,
   isolating the secreted biologically active MIP from the culture medium.

\* \* \* \* \*